US008617569B2

(12) United States Patent
Binder

(10) Patent No.: US 8,617,569 B2
(45) Date of Patent: Dec. 31, 2013

(54) TREATMENT OF MIGRAINE HEADACHE WITH DIFFUSION OF TOXIN IN NON-MUSCLE RELATED FORAMINAL SITES

(76) Inventor: William J. Binder, Beverly Hills, CA (US)

( * ) Notice: Subject to any disclaimer, the term of this patent is extended or adjusted under 35 U.S.C. 154(b) by 0 days.

(21) Appl. No.: 13/478,602

(22) Filed: May 23, 2012

(65) Prior Publication Data

US 2013/0236444 A1 Sep. 12, 2013

Related U.S. Application Data

(60) Provisional application No. 61/609,817, filed on Mar. 12, 2012.

(51) Int. Cl.
*A61K 39/08* (2006.01)
(52) U.S. Cl.
USPC .................. 424/239.1; 435/252.7; 514/18.3
(58) Field of Classification Search
None
See application file for complete search history.

(56) References Cited

U.S. PATENT DOCUMENTS

| 5,714,468 | A | 2/1998 | Binder |
| 5,721,215 | A | 2/1998 | Aoki et al. |
| 6,458,365 | B1 | 10/2002 | Aoki et al. |
| 7,655,244 | B2 | 2/2010 | Blumenfeld |
| 7,704,511 | B2 | 4/2010 | Turkel et al. |
| 7,981,433 | B2 | 7/2011 | Blumenfeld |
| 2010/0227822 | A1* | 9/2010 | Blumenfeld .................... 514/12 |

OTHER PUBLICATIONS

Andrew Blumenfeld, et al. "Method of Injection of OnabotulinumtoxinA for Chronic Migraine: A Safe, Well-Tolerated, and Effective Treatment Paradigm Based on the PREEMPT Clinical Program", Headache, 2010 American Headache Society, ISSN 0017-8748; doi: 10.111/j.1526-4610.2010.01766.x, Wiley Periodicals, Inc.
Lidija Bach-Rojecky, et al., "Central Origin of the Antinociceptive Action of Botulinum Toxin Type A", Pharmacology, Biochemistry and Behavior 94 (2009) 234-238, Elsevier, Inc.
Ritu Bahl, "Local Anesthesia in Dentistry", Anesth Prog 51:138-142 (2004), American Dental Society of Anesthesiology.
Stanley F. Malamed, et al., "Intraoral Maxillary Nerve Block: An Anatomical and Clinical Study", Anesthesia Progress, Mar./Apr. 1983, pp. 44-48.

* cited by examiner

*Primary Examiner* — Jon P Weber
*Assistant Examiner* — Teresa E Knight

(57) ABSTRACT

A method for treating a patient with migraine headache includes administering to the patient a therapeutically effective amount of an invertebrate presynaptic neurotoxin in a pharmaceutically safe form. The administration includes extramuscular injection of the neurotoxin to emerging nerve points including foraminal sites for enabling neurotoxin access to concentrated nerve bundles at exit points of the foramina.

9 Claims, 1 Drawing Sheet

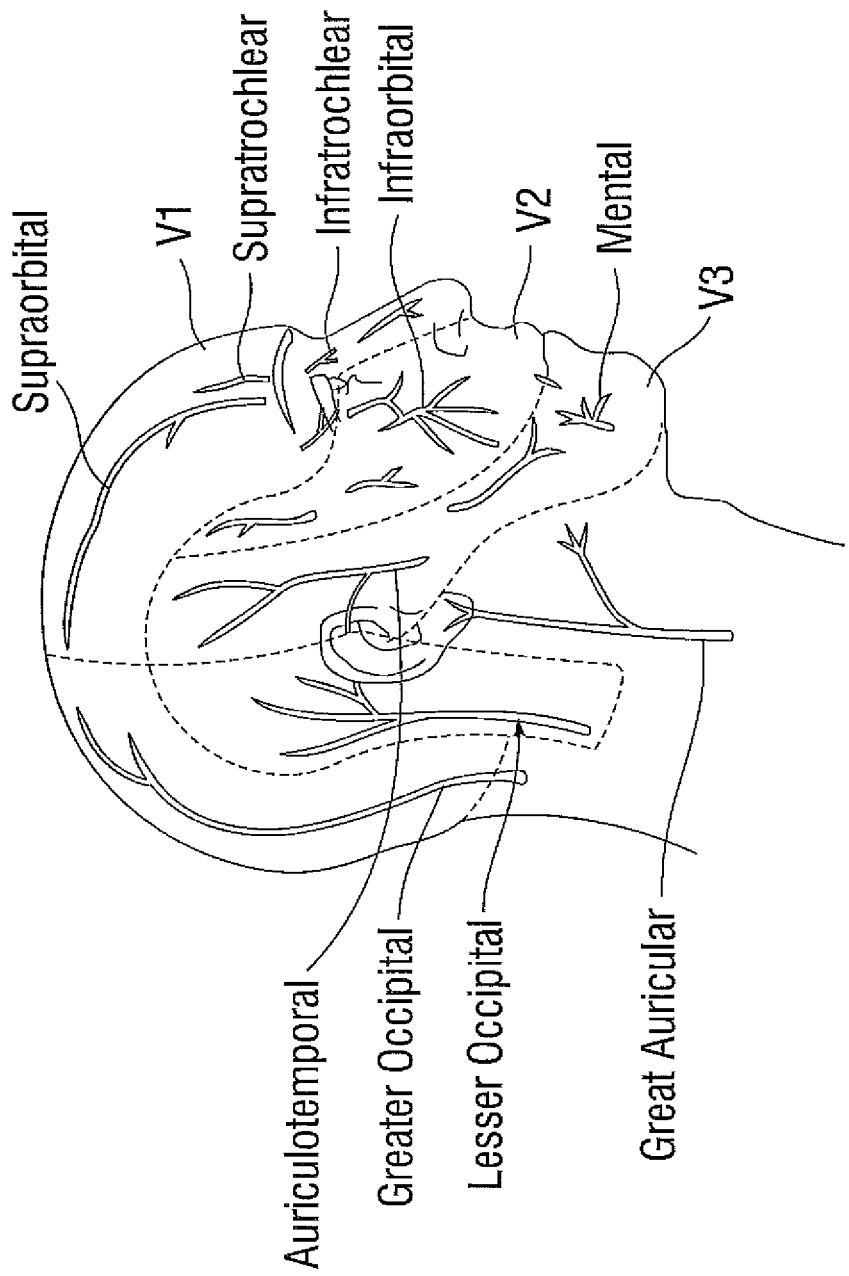

TREATMENT OF MIGRAINE HEADACHE WITH DIFFUSION OF TOXIN IN NON-MUSCLE RELATED FORAMINAL SITES

CROSS REFERENCE TO RELATED APPLICATIONS

This patent application claims the benefit of U.S. Provisional Patent Application 61/609,817 which was filed on Mar. 12, 2012.

Botulinum toxins have been used to treat migraine. This is well established in the art. By way of example only, see U.S. Pat. Nos. 5,714,468, 5,721,215, 6,458,365, 7,655,244, 7,704,511, and 7,981,433. All of these references are to be incorporated herewith in their entirety. These patents include: Binder; Botulinum toxin injections to the head for migraine, Blumenfeld; Botulinum toxin injections to the sphenopalatine ganglion, nasal approach and vascular approach, suture line technique (these are not foramina or exit points); Aoki; Tension type headache treatment with Botulinum toxin, and Turkel; 31 sites as for the FDA approved protocol for chronic migraine.

Heretofore, onabotulinumtoxinA has been FDA approved for treatment of migraine headache. The dose used is 155 to 195 units, with a dilution of 2 cc per 100 units of onabotulinumtoxinA. Doses ranging from 25 units to 260 units have been used to treat various headache disorders. These have involved intra-muscular injections in fixed sites and follow the pain sites.

Botulinum toxin side effects are usually due to local diffusion to surrounding muscles producing unwanted weakness.

SUMMARY OF THE INVENTION

The present invention is directed to treating migraine headaches with Botulinum toxin (and/or endopeptidase) by adjusting the toxin concentration and volume to establish optimum diffusion of toxin in non-muscle related areas of the head and neck, or exit points of nerves therein. The improvement avoids side effects such as muscle paralysis and reduces doses overall by use of high concentration/low volume injections at nerve exit points which also results in reduction of injection pain due to less rapid tissue expansion upon injection.

In general, the present invention aims to minimize any side effects present with prior injection techniques and uses a novel injection approach to achieve this goal. In addition, this invention aims to increase the efficacy across multiple headache types including chronic and episodic migraine, post-traumatic headache, post-craniotomy headache, tension type headache and medication overuse headache. This invention focuses the medication on the sites of maximal benefit; i.e., the trigemino-cervical nerves.

This invention uses the same methods of administration described in the procedures above to deliver endotoxins to the same sites. Endotoxins do not cause muscle weakness as they are targeted to sensory nerves, however the current technique of intra-muscular injections can still cause side effects related to needle trauma of muscle and the need to do multiple injections.

In general, a method for treating a patient with migraine headache in accordance with the present invention includes administering to the patient a therapeutically effective amount of an invertebrate presynaptic neurotoxin in a pharmaceutically safe form. The administration includes extra-muscular injection of the neurotoxin to emerging nerve points in the head and neck for enabling the neurotoxin access to concentrated nerve bundles at exit points of the foramina.

More specifically, the administration includes the extra-muscular injection of diluted Botulinum toxin.

Still more particularly, the Botulinum toxins may be Botulinum Toxin A, B, C, D, E, F, and G. The preferred Botulinum toxin is Botulinum toxin A and more preferably onabotulinumtoxinA.

BRIEF DESCRIPTION OF THE DRAWINGS

The advantages and features of the present invention will be better understood by the following description when considered in conjunction with the accompanying drawing, in which:

FIG. 1 illustrates suitable nerve exit points in the head and neck.

DETAILED DESCRIPTION

Emerging nerve points which include foraminal injection sites and foraminal injection sites deep in the muscle layer allows Botulinum toxin access to the concentrated nerve bundles at the exit points and thus lower doses with improved efficacy and less side effects and adverse events and can be achieved. The cervical plexus emerges from the posterior portion of the sternocleidomastoid muscle and injections at this site can encompass the entire distribution of the cervical plexus. The dilution for these injections is about 1 cc per 100 units of Botulinum toxin. The concentrated solution prevents diffusion to local muscle and the accurate needle placement allows the medication to be delivered to the site where it will most effective.

With reference to FIG. 1, sensory branches of the trigeminal nerves (ophthalmic V1, maxillary V2 and mandibular V3) leave the skull through three separate foramina; in the following order: the superior orbital fissure, the foramen rotundum, and the foramen ovale.

V1 carries information from the scalp (forehead to vertex) upper eyelid and eye, nose and nasal mucosa, meninges and frontal sinuses.

V2 carries information from lower eyelid, cheek, upper lip, dentition, mouth meninges and sinuses (ethmoid and sphenoid).

V3 carries information from lower lip, dentition, jaw, external ear and meninges.

Note all 3 divisions supply the meninges.

The pain modality is carried by unmyelinated C fibers within these trigeminal nerves to the trigeminal nucleus caudalis and then in the trigemino-thalamic or quinto-thalamic tract to the thalamus (VPL and VPM nuclei).

The foraminal anatomy is as follows:

Frontal region—supraorbital foramen—supra-orbital nerve

Frontal region—supratrochlear foramen—supratrochlear nerve

Maxilla—incisive foramen—nasopalatine nerve (Septum)

Palatine—greater and lesser palatine foramen—greater and lesser palatine nerves

Maxilla—Inferior orbital fissure/foramen—zygomatic and infra-orbital nerves and orbital branch of the pterygopalatine ganglion (SPG).

Mandibular—the mental foramen—the mental nerve and more proximal inferior alveolar nerve.

At this point the maxillary nerve gives branches to the sphenopalatine ganglion. Among the nerves that pass through the sphenopalatine ganglion is the nasopalatine nerve (also called the long sphenopalatine nerve) that passes along the nasal septum and emerges at the incisive foramen on the anterior hard palate. It supplies sensation to the gingival soft tissues of the anterior hard palate. The greater and lesser palatine nerves also pass through the sphenopalatine ganglion and course through the greater and lesser foramina, respectively. The greater palatine nerve innervates the palatal mucoperiosteum and the gingiva from the molars to the area near the cuspid region that abuts tissue supplied by the nasopalatine nerve. The lesser palatine nerve supplies the tissues of the soft palate and uvula. The maxillary nerve also gives rise to the posterior superior alveolar nerve, which supplies sensation to the buccal gingiva and periodontium adjacent to the maxillary molar teeth and the pulps of all molar teeth except the mesio-buccal pulp of the upper first molar. That mesio-buccal pulp is supplied by another branch of the maxillary nerve, the middle superior alveolar nerve, which also innervates the pulps, buccal gingiva, and peridontium of the maxillary premolars. The final branch of the maxillary nerve, the anterior superior alveolar nerve, supplies the pulps of the upper incisors and cuspid along with the associated buccal gingiva and periodontium.

The mandibular division exits the skull through the foramen ovale to enter the infratemporal fossa where it then divides into the anterior and posterior divisions. The anterior division has sensory branches: the long buccal nerve that supplies the buccal mucosa and the gingiva adjacent to the lower molar and second premolar teeth. The posterior division branches to give the auriculotemporal, lingual, and inferior alveolar dental nerves. The lingual nerve innervates the lingual gingiva, floor of the mouth, and anterior two-thirds of the tongue. The inferior alveolar nerve supplies sensation to the pulp and periodontium of all the molar and premolar teeth. Near the mental foramen, the inferior alveolar nerve branches into the incisive and mental nerves. The mental nerve innervates the buccal gingiva and the mucosa from the mental foramen forward to the midline, including the skin of the lower lip and chin. The incisive nerve supplies the pulps of the first premolar, canine, and incisor teeth.

The aponeurotic fascia extends from the frontalis to the occipitalis muscles.

However, for the foraminal and emerging nerve bundle injections, a 1 cc dilution is used to prevent diffusion to surrounding muscles. The lower amount of volume of diluent injected also causes less rapid tissue expansion upon injection and thus results in less pain than would be the case with injection of higher volumes of diluents conventionally used.

Clinical Examples:

Case 1

43 year old woman, with a long standing history of migraine, suffers with headache on twenty (20) days out of each month and requires triptan medication on twelve (12) days out of each month to try and control her more disabling headaches. She meets criteria for chronic migraine complicated by medication overuse headache. She fails to respond to numerous preventive medications such as Topiramate and Propranolol. She is treated with onabotlinumtoxinA using the PREEMPT injection protocol with fixed sites and follow-the-pain injections. Total dose given is 195 units. She develops neck pain, brow ptosis and little improvement in her headache frequency after three (3) treatment cycles.

She is then treated with the injection protocol as outlined in this invention.

1 cc dilution: 100 units of Botulinum Toxin A in 1 cc saline
Orbital ridge supra-medial angle over supra-trochlear and supra-orbital nerves 5 units each side Infraorbital foramen 5 units each side Mental foramen 5 units each side Posterior aspect, mid-section of sternocleidomastoid muscle 5 units each side Occipital foramen 5 units each side Auriculotemporal nerve just anterior and inferior to the tragus 5 units each side Intra-oral muscosal injection superior to second molar intra-oral 5 units each side Total dose given 60 units.

The patient does not develop neck weakness or pain as the neck musculature is not injected. The patient does not develop brow ptosis as the frontalis muscle is not injected. The patient experiences less pain from the injections than from conventional treatment. The patient's migraine headache symptoms improve with less frequency and less intensity.

Lower dosing of onabotulinumtoxinA is used as the medication is delivered in a focus where it will have the most benefit; i.e.: no unnecessary flooding of medication and volume of diluents to unwanted sites.

Case 2

60 year old woman with frequent episodic migraine and severe needle phobia has been treated with onabotulinumtoxinA using the PREEMPT protocol in the past. Due to her needle phobia her method of treatment is changed with a focused delivered method of onabotulinumtoxinA at emerging nerve points. This method is chosen to limit side effects from intra-muscular injections and to achieve a high level of efficacy with the fewest possible needle insertions. The patient is treated lying down. Onabotulinumtoxin A is diluted with 1 cc of normal saline per 100 units; i.e.: 0.1 cc contains 10 units. At each injection site only 0.05 cc is delivered. The lower volume of onabotulinumtoxinA injection produces less discomfort due to less rapid expansion of tissue. A 31-gauge half-inch needle is used for administration. However a 30 gauge or 32 gauge needle can also be used. The following sites are injected:

The orbital bony ridge is palpated. Midway along the ridge the supra-orbital notch is palpable. This is a tender point and correlates with the emerging supra-orbital nerve. After injecting at this site the ridge is palpated over the supero-medial aspect, just adjacent to the nose, a tender point is located which correlates to the supra-trochlear nerve. This site is injected. The dosing at these two sites is: Orbital ridge supra-medial angle over supra-trochlear and supra-orbital nerves 5 units (0.05 cc) each site and this is repeated on the opposite side. Total dose given at these locations is 20 units. Infra-orbital ridge is palpated. In line with the mid-pupillary point vertical line is followed inferiorly to a tender region located just below the orbital margin. This correlates with the emerging infra-orbital nerve. The dose injected at this site is 5 units (0.05 cc) and this is repeated on the opposite side. Total dose given at these sites is 10 units.

The patient is asked to rotate her head towards her shoulder and tilt the head downwards towards the chest. This activates the sternomastoid muscle. The muscle is palpated between the examiner's thumb and index fingers.

The examiner grips this muscle as the patient rotates the head back to the mid-line position. The posterior border of the muscle is palpated, and in the mid-section of the sternomastoid muscle a tender point is localized. This correlates with the emerging cervical rami, 10 units (0.1) is injected at this site and repeated on the opposite side. The total dose given at these sites is 20 units.

The Occipital foramen is palpated mid-way along the nuchal ridge between the occipital protuberance and the mastoid process. This is also a tender point and correlates to the emergence of the greater occipital nerve, 5 units of onabotulinumtoxinA, 0.05 cc are injected on each side in the same fashion. The total dose given at these sites is 10 units.

The emerging Auriculo-temporal nerve is injected just (a finger tip) anterior and inferior to the tragus and 5 units (0.05 cc) of onabotulinumtoxinA are given on each side. The total dose given to these sites is 10 units.

The total dose given to the patient for this treatment is 70 units.

The smaller needle size, the more concentrated onabotulinumtoxinA solution and the focused injection sites limit the pain associated with administration. The procedure is well tolerated and migraine headache symptoms are successfully treated.

Although there has been hereinabove described a specific treatment of migraine headache with diffusion of toxin in non-muscle related areas of the head and administration of neurotoxin to emerging nerve points including but not limited to foraminal sites, for enabling a more concentrated solution of the neurotoxin access to concentrated nerve bundles at exit points of the foramina in accordance with the present invention for the purpose of illustrating the manner in which the invention may be used to advantage, it should be appreciated that the invention is not limited thereto. Further, the invention illustratively disclosed herein suitably may be practiced in the absence of any element which is not specifically disclosed herein. Accordingly, any and all modifications, variations or equivalent arrangements that may occur to those skilled in the art, should be considered to be within the scope of the present invention as defined in the appended claims.

What is claimed is:

1. A method for treating a human patient with migraine headache, said method comprising: administering to the patient a therapeutically effective amount of a neurotoxin which is a Botulinum toxin or a tetanus toxin in a pharmaceutically safe form; and the administration comprising extramuscular injection of the neurotoxin to unmyelinated C fibers at emerging nerve exit points, wherein said nerve exit points are one or more of the Great auricular, Auriculotemporal, Supraorbital, Supratrochlear, Infratrochlear, Infraorbital or Mental nerve exit points.

2. The method of claim 1, wherein the neurotoxin is Botulinum toxin.

3. The method of claim 2, wherein the Botulinum toxin is Botulinum toxin A.

4. The method of claim 3, wherein the Botulinum toxin A is onabotulinumtoxinA.

5. The method of claim 2, wherein the Botulinum toxin is Botulinum toxin B.

6. The method according to claim 2, wherein the Botulinum toxin is administered in a concentrated form of about 1 cc of normal saline to 100 units of Botulinum toxin thereby causing less rapid tissue expansion upon injection resulting in less pain.

7. The method according to claim 1, wherein the neurotoxin comprises an Endotoxin.

8. The method of claim 7, wherein the Endotoxin is an endopeptidase derived from Botulinum toxin.

9. The method of treating a human patient with migraine headache, said method comprising administering to the patient a therapeutically effective amount of Botulinum toxin A in a pharmaceutically safe form; the administration comprising extramuscular injection of the Botulinum toxin A in a concentrated form of about 1 cc per 100 units of botulinum toxinA to one or more of the Great auricular Auriculotemporal, Supraorbital, Supratrochlear, Infratrochlear, Infraorbital, and Mental nerve exit points.

* * * * *